US00PP21666P3

(12) United States Plant Patent
Higaki

(10) Patent No.: US PP21,666 P3
(45) Date of Patent: Jan. 25, 2011

(54) ***HYDRANGEA* PLANT NAMED 'CARINA'**

(50) Latin Name: *Hydrangea macrophylla (Thunb.)*
Varietal Denomination: Carina

(75) Inventor: Harrison M. Higaki, San Mateo, CA (US)

(73) Assignee: Bay City Flower Co., Half Moon Bay, CA (US)

( * ) Notice: Subject to any disclaimer, the term of this patent is extended or adjusted under 35 U.S.C. 154(b) by 0 days.

(21) Appl. No.: 12/381,851

(22) Filed: Mar. 17, 2009

(65) Prior Publication Data

US 2010/0242144 P1 Sep. 23, 2010

(51) Int. Cl.
*A01H 5/00* (2006.01)

(52) U.S. Cl. ..... Plt./250
(58) Field of Classification Search ..... Plt./250
See application file for complete search history.

*Primary Examiner*—Annette H Para
(74) *Attorney, Agent, or Firm*—James R. Cypher; Charles R. Cypher

(57) ABSTRACT

A new and distinct cultivar of *Hydrangea macrophylla* (Thunb.) named 'Carina' originated as a found plant in a cultivated area of 'Orion'. The cultivar 'Carina' has a R.H.S. 68 A (red-purple group) bi-color pigmentation pattern on its sepals at maturity, with the pigmentation giving way to non-pigmented margins and is distinguished from other similar cultivars of which the inventor is aware by its stable sepal color pattern, its sturdy growth habit, and small leaves. 'Carina' has large showy inflorescences, having both sepalous and non-sepalous florets, with the sepalous florets hiding the non-sepalous florets.

4 Drawing Sheets

Botanical classification: *Hydrangea macrophylla* (Thunb.) 'Carina'.

Variety denomination: 'Carina'.

BACKGROUND OF THE INVENTION

This invention relates to a new and distinct cultivar of the Saxifragaceae family. The botanical name of the plant is *Hydrangea macrophylla* (Thunb.) 'Carina'.

The new cultivar originated as a found plant in a field of *Hydrangea macrophylla* (Thunb.) 'Orion'

The variety 'Carina' has pigmented sepals like the parent 'Orion', and is typically grown under soil conditions with pH conditions that produce pink pigmentation.

The new variety was first noticed, because of its relatively stronger stems and upright growth habit. Unlike its parent 'Orion', the new variety's pigmentation pattern remains stable. The new variety has small leaves, and a stronger, upright growth habit, although for commercial sale, it still needs to be staked. The new variety also has good breaking characteristics. When meristems are pinched, multiple lateral shoots grow out producing multiple inflorescences per plant.

The new cultivar 'Carina' has been successfully asexually reproduced under controlled environmental conditions at a nursery in Half Moon Bay, Calif. under the direction of the inventor through three generations with its distinguishing characteristics remaining stable.

'Carina' is distinguished from other bi-color varieties of *Hydrangea* of which the inventor is aware by its small leaves, relatively strong stems, exceptional branching characteristics when pinched, and stable pigmentation pattern. The sepals are predominantly pink with narrow (approximately 2 mm), delineated white margins.

TABLE 1

| | New Variety 'Carina' | U.S. Plant Pat. No. 9,499 'Frau Katsuko' | U.S. Plant Pat. No. 9,510 'Frau Machiko' |
|---|---|---|---|
| Relative Height | Compact | Compact | Compact |
| Leaf size | 4.625" long, 3.25" wide. | 5.3" long, 3.3" wide. | 5.3" long, 3.6" wide. |
| Stem strength | Good but still needs to be staked for commercial sale. | Very good. Does not need to be staked. | Good, but still needs to be staked for commercial sale. |
| Pigmentation Pattern | Narrow (2 mm) R.H.S. 155 D (white group) margins, otherwise R.H.S. 68 A (red-purple) group. | Wide (5 mm) white margins, otherwise blue or red depending on pH of soil | Predominately white with blue or pink pigmentation radiating from the middle veins of the sepals, depending on pH of soil. Cruciform appearance. |
| Stability of Pigmentation Pattern | Very stable | Irregular | Stable |
| Relative ease of branching when pinched | Excellent | Good | Good |

| | U.S. Plant Pat. No. 10,371 'Frau Nobuko' | U.S. Plant Pat. No. 10,372 'Frau Taiko' |
|---|---|---|
| Relative Height | Compact, but growth regulators needed for commercial sale | Compact, but growth regulators need for commercial sale. |
| Leaf size | 4.1" long, 2.8" wide | 4.7" long, 4.1" wide |
| Stem strength | Very good. Does not need to be staked. | Very good. Does not need to be staked. |

TABLE 1-continued

| | | |
|---|---|---|
| Pigmentation Pattern | Wide, irregular (5 mm) white margins, otherwise blue or pink depending on pH of soil | Narrow R.H.S. 155 A (white group) border, with R.H.S. 88 B (violet group) or R.H.S. 82 B (purple-violet group) pigmentation depending on pH of soil. |
| Stability of Pigmentation Pattern | Irregular, white fades as sepals age. | Stable |
| Relative ease of branching when pinched | Good | Good |

Asexual reproduction was first accomplished when vegetative cuttings were taken from the initially selected plants. Examination of asexually reproduced, successive generations grown in a nursery at Half Moon Bay, Calif. show that the combination of characteristics as herein disclosed for 'Carina' remains firmly fixed through three generations.

DESCRIPTION OF THE DRAWINGS

The accompanying drawings consist of color photographs that show the typical plant form, including the inflorescence, foliage, and sepals.

DESCRIPTION OF THE NEW PLANT

Figure 1:
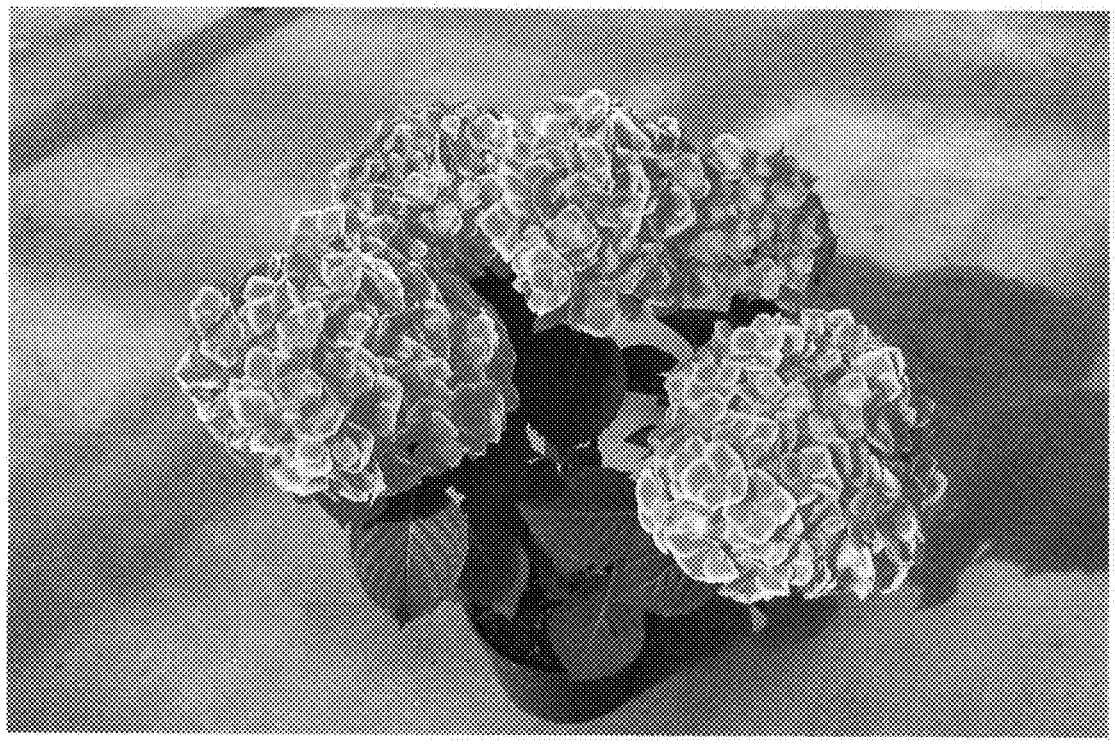
FIG. 1 is a top view of the entire plant. The plant has a compact growth habit, dark green foliage, inflorescence, and bi-color, pigmented sepals. The particular plant shown has multiple panicles.
Figure 2:
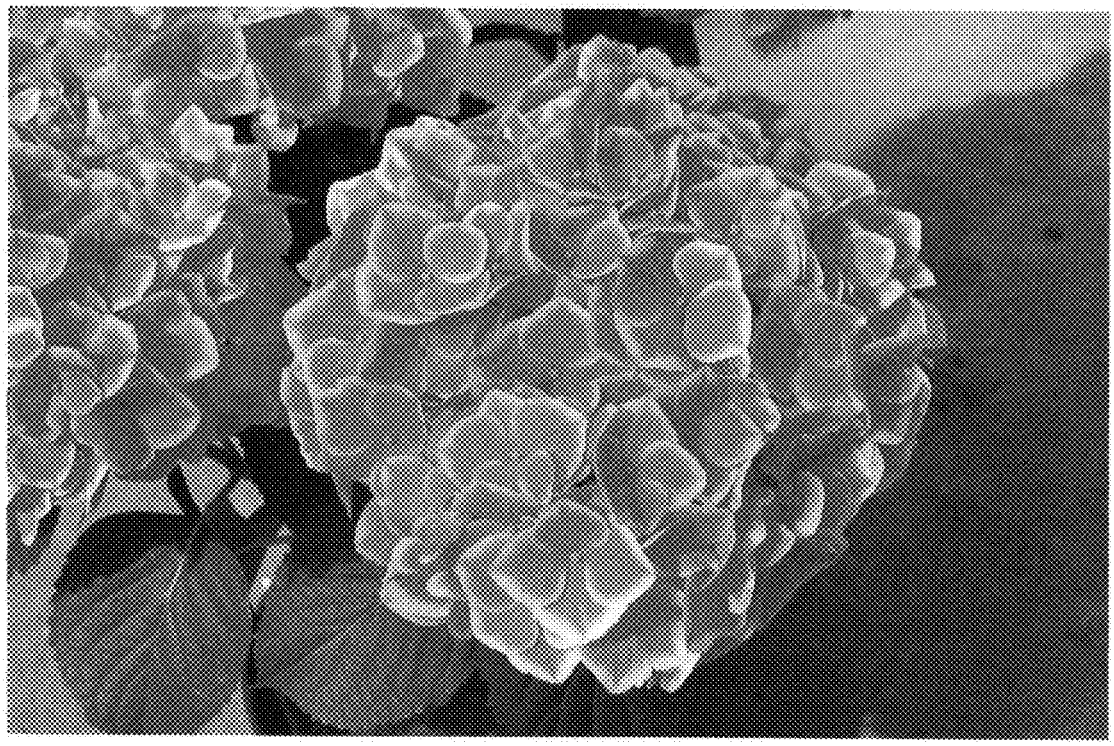
FIG. 2 is a close-up view of a panicle of the new variety, showing opened, sepalous florets.
Figure 3:
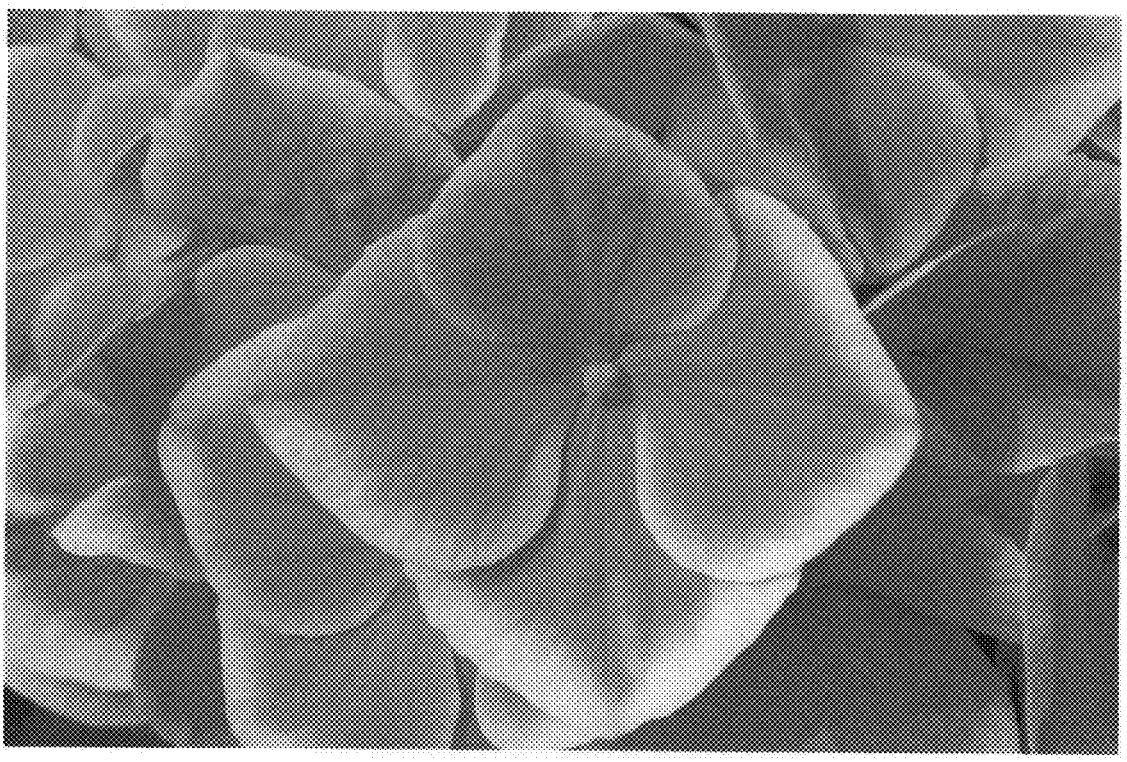
FIG. 3 is a close-up view of a mature floret of the new variety.
Figure 4:
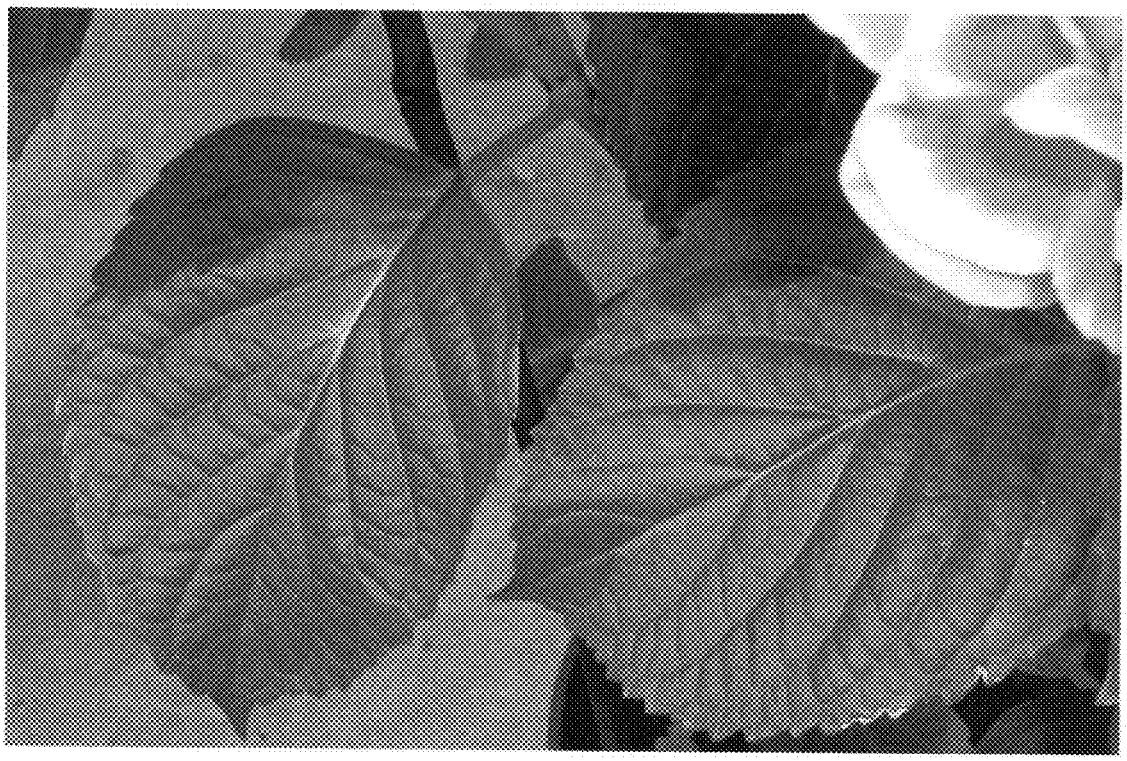
FIG. 4 is a close-up view of the adaxial surface of a mature leaf.
Figure 5:
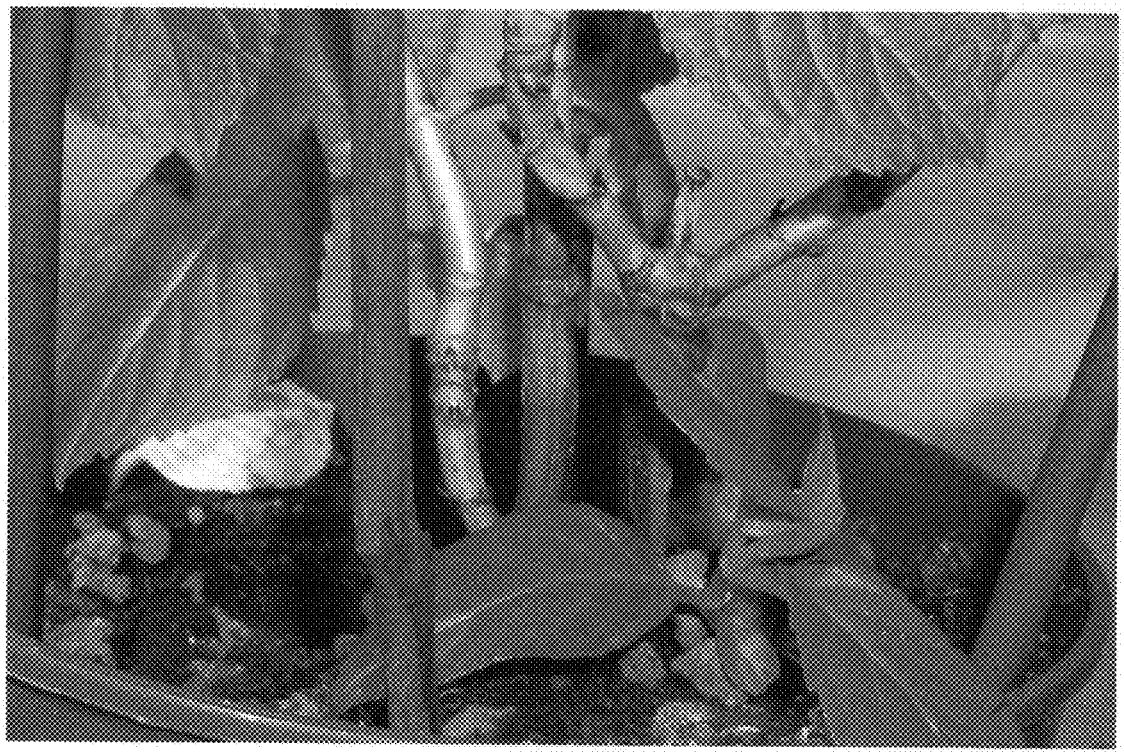
FIG. 5 is a close-up view of the base of the stem.
Figure 6:
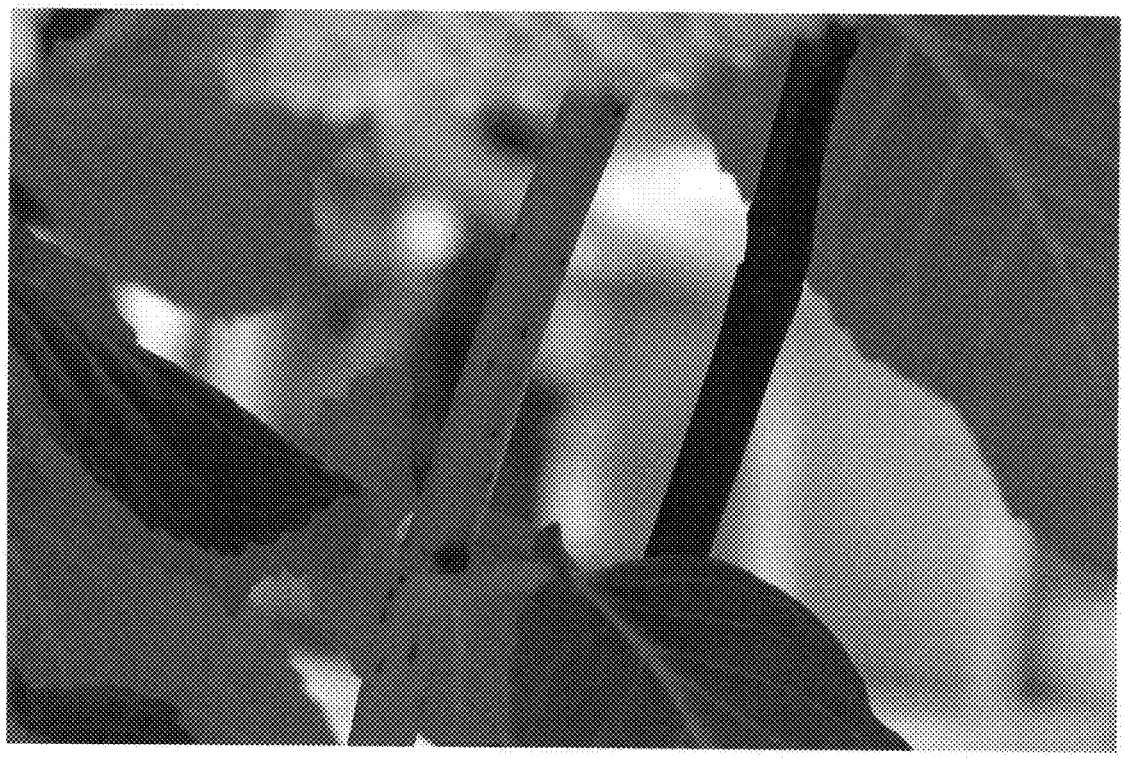
FIG. 6 is a close-up view of an upper portion of the stem of the plant.
Figure 7:
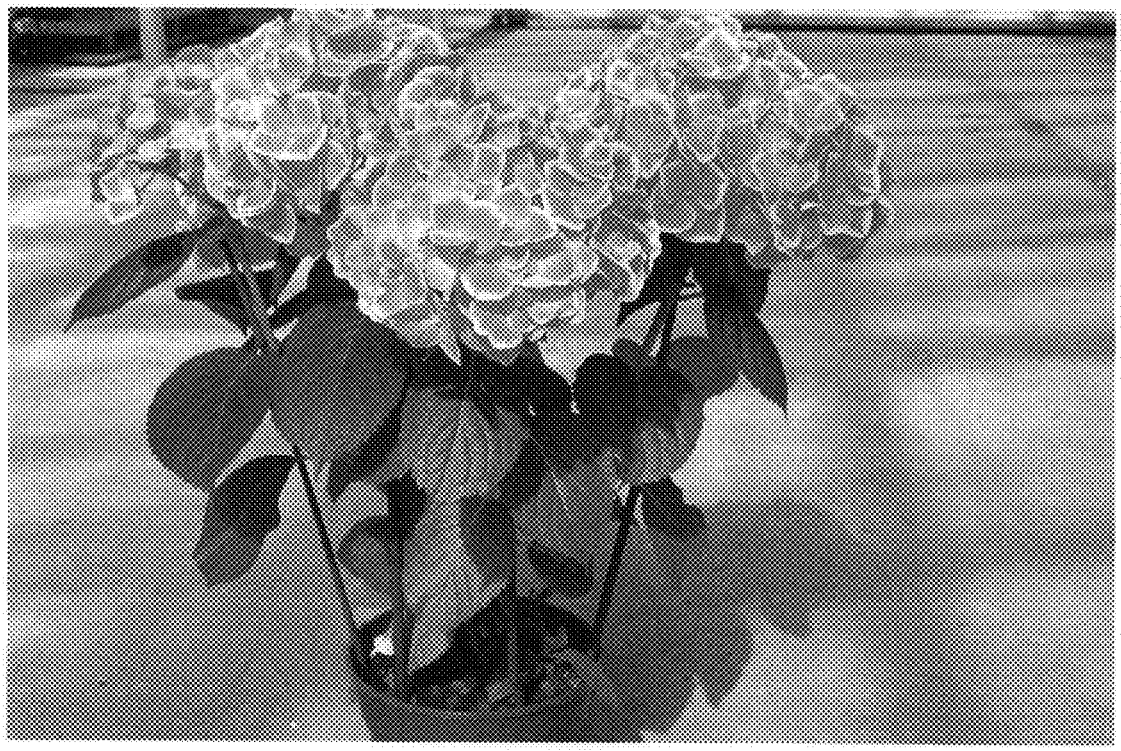
FIG. 7 is a view of the entire plant.

The plants shown in the figures started out as cuttings, taken from the stem of a grown plant. The cuttings were placed in a 6" pot with *hydrangea* soil that would produce pink pigmentation in *Hydrangeas* that have pigmentation in their sepals. Stems of the plant were staked.

'Carina' has not been observed under all possible environmental conditions. The phenotype may vary significantly with variations in environment such as temperature, light intensity and day length. Color determinations were made with The Royal Horticultural Society (R.H.S.) Colour Chart.

THE PLANT

Origin: Found in a cultivated area of *Hydrangea macrophylla* (Thunb.) 'Orion'.

*Botanic classification.*—*Hydrangea macrophylla* (Thunb.) 'Carina'.

Form: Upright, compact shrub. A typical plant with a mature inflorescence that is ready for sale at approximately nine months, and has been staked, is approximately 18" high, has 4 to 6 inflorescences after being pinched, and has a diameter of 18" when grown in a 6" pot with appropriate soil amendments. Bottom 1.5 to 4 inches of the stems are woody.

Growth: Upright growth habit. Inflorescence is large. The plant branches easily when pinched.

Stems: Lenticels are present. Stems become woody as they age. The color of typical young stems and young lateral branches is R.H.S. 145 A (yellow-green group). Woody stems are R.H.S. 199 D (grey-brown group). The lenticels are R.H.S. 182 A (greyed-red group)

Foliage: Abundant. Leaves are opposite on stem and lateral branches.

*Shape of leaf.*—Elliptic with acute base and apex. Margins are serrate.

*Texture.*—Glabrous; veins dominate on the underside of the leaf and are sunken on the leaf surface.

*Color.*—Mature leaves have an upper side that is R.H.S. 137 A (green group), and an under side that is R.H.S. 147 B (yellow-green group). The upper side of younger leaves can be a little darker at R.H.S 139 A (green group). The veins of mature leaves are R.H.S. 145 C (yellow-green group) whether viewed from the top or the bottom of the leaf. Leaves are pinnately veined. The midvein and veins branching off the midvein are large and prominent on the underside of the leaves. Large leaves are 4.625 inches long (not including the petiole) and 3.25 inches wide. Smaller leaves are 4 inches long and 2.75 inches wide. Petiole lengths range from 0.75 to 1 inches.

BUDS

Form: Globose with 4 to 5 connate petals (sometimes 3). The inflorescence contains both sepalous and non-sepalous florets, with the sepalous florets dominating the inflorescence. Buds have a diameter of approximately 5 mm at maturity. Very young floret buds are R.H.S. 145C (yellow-green group). Mature florets are primarily R.H.S. 68A (red-purple group).

Aspect: Smooth.

Arrangement: Borne on branched panicles.

INFLORESCENCE

Form: Paniculate. Terminal. As many as 200 or more individual flowers (florets) per inflorescence. Both sepalous florets and non- sepalous florets borne on same panicle. Flowers do not produce a fragrance. The peduncle or panicle for the inflorescence is branched, strong and upright. The uppermost portions of the pedicels for the individual florets in a mature infloresence are predominately R.H.S. 69 A (red-purple group) at maturity.

Size of inflorescence: Large. Individual inflorescence size is dependent on the number of florets. A typical inflorescence can grow as large as 8" in diameter, and 4" high.

Shape: Clusters of numerous small florets; sepalous florets are flat and overlapping one another. Sepals are persistent.

Appearance: Showy.

FLORETS

*General.*—The non-sepalous florets at the center of the inflorescence open first. Sepalous florets are perfect and complete, although petals, stamens and ovary generally fall off. Corolla: Generally there are 4 petals that are R.H.S. 68 A (red-purple group).

*Stamens.*—8- 10 stamens. Pollen is R.H.S. 8D (yellow group). Plant produces abundant pollen. Filament is R.H.S. 69 A (red-purple group) and approximately 3 mm long. Anther is 1 mm long and is regular and basally attached.

*Stigma.*—Generally, a three-pronged stigma on one pistil per floret. Stigma is R.H.S. 69 A (red-purple group) and protrudes from the ovary approximately 1 mm.

*Ovary.*—Ovary is R.H.S. 145 C (yellow-green group) when young, becoming closer to color of stigma as the floret matures. Ovary is partially inferior.

Sepalous florets:

*General.*—Veins dominate on the underside of the sepals.

*Number of sepals.*—4 or 5 sepals per floret, usually 4, and sometimes 3.

*Aspect of sepals.*—Smooth and glaucescent.

*Shape of sepals.*—Reniform with acuminate apex. Edges often wavy when the floret is young.

*Size of sepals.*—As the florets mature, the sepals enlarge and overlap each other. Usually 1 dominant sepal, 2 smaller but equally-sized sepals, and 1 small sepal. Largest sepal at maturity is typically 24 mm long and 29 mm wide, the medium sized sepals are typically 22 mm long by 25 mm wide, and the smallest sepals are typically 21 mm long and 22 mm wide.

*Coloration of sepals.*—At maturity the sepals have narrow (approximately 2 mm) R.H.S. 155 D (white group) margins with the remainder of the sepals being R.H.S. 68 A (red-purple) group. Young sepals are R.H.S.145 C (yellow-green group). Mature sepals are R.H.S. 69 A (red- purple group).

Fruit: None.

I claim:

1. A new and distinct *Hydrangea macrophylla* (Thunb.) plant named 'Carina' substantially as herein shown and described.

* * * * *